(12) United States Patent
Takayama et al.

(10) Patent No.: US 6,767,743 B2
(45) Date of Patent: Jul. 27, 2004

(54) METHOD AND AN APPARATUS FOR GENERATING SHOCKWAVE, A METHOD AND AN APPARATUS FOR ACCELERATING PARTICLES, AN APPARATUS FOR DELIVERING DRUGS, AND A METHOD AND AN APPARATUS FOR DELIVERING DNA

(76) Inventors: Kazuyoshi Takayama, 6-9-7, Oritate, Aoba-ku, Sendai-shi, Miyagi (JP); Akira Takahashi, 7-16-8, Koriyama, Taihaku-ku, Sendai-shi, Miyagi (JP); Jun Kawagishi, 1-22-4, Kunimigaoka, Aoba-ku, Sendai-shi, Miyagi (JP); Goparan Jagadeesh, YoshidaApart Ha-1, 2-3-30, Komegafukuro, Aoba-ku, Sendai-shi, Miyagi (JP); Takashi Yoshimoto, 12-2, Tsunogoro, 1-chome, Aoba-ku, Sendai-shi, Miyagi (JP)

( * ) Notice: Subject to any disclaimer, the term of this patent is extended or adjusted under 35 U.S.C. 154(b) by 0 days.

(21) Appl. No.: 10/099,072

(22) Filed: Mar. 15, 2002

(65) Prior Publication Data

US 2003/0104627 A1 Jun. 5, 2003

(51) Int. Cl.[7] ............................................. C12N 15/64
(52) U.S. Cl. ..................... 435/459; 435/471; 435/285.1; 435/285.2; 435/285.3; 435/470; 102/202.5; 102/202.7; 102/217
(58) Field of Search ................................ 435/459, 470, 435/471, 285.1, 285.2, 285.7; 102/202.5, 202.7, 217

(56) References Cited

U.S. PATENT DOCUMENTS 5,080,016 A * 1/1992 Osher
5,206,455 A * 4/1993 Williams et al.
6,386,108 B1 * 5/2002 Brooks et al.

* cited by examiner

*Primary Examiner*—James Ketter
(74) *Attorney, Agent, or Firm*—Jordan and Hamburg LLP

(57) ABSTRACT

Method and apparatus for accelerating micro particles for use in delivering DNA or a solid drug in which a shockwave is generated by applying a short pulse energy to a surface of a metal foil to be absorbed and cause vaporization and plasmatization of the metal foil. A jet is generated by a sudden expansion of metal gas and thereby the shockwave is generated on a surface of an opposite side of the metal foil on which the micro particles are arranged.

15 Claims, 3 Drawing Sheets

METHOD AND AN APPARATUS FOR GENERATING SHOCKWAVE, A METHOD AND AN APPARATUS FOR ACCELERATING PARTICLES, AN APPARATUS FOR DELIVERING DRUGS, AND A METHOD AND AN APPARATUS FOR DELIVERING DNA

FIELD OF THE INVENTION

The present invention relates to a method and an apparatus for generating a shockwave, a method for accelerating particles, a particle accelerating apparatus, a drug delivery apparatus, and/or a method and an apparatus for delivering DNA.

BACKGROUND OF THE INVENTION

As molecular biology has recently discovered the cause of many diseases, the importance of gene therapy will expectedly still increase. The actual condition of arteriosclerosis is the inflammatory, hyperplastic reaction of the endothelium and/or smooth muscle of vessels against damage, and is considered to be a good application for the gene therapy. However, the delivery of DNA into cells requires virus vector, ribosome and others. With the usage of these means, infection and potential carcinogenesis are serious risk factors for the application of gene therapy. Also, low efficiency of the DNA delivery is an obstacle.

For instance, stable gene growth can be achieved with retrovirus, but the efficiency of the DNA is low and the risk of corcinogenesis cannot be avoided. Adenovirus delivers DNA at a higher efficiency rate, but immunoreaction and crytotoxicity is reportedly induced with this means, and the risk of delivering extraneous DNA to unintended organs has been pointed out. DNA delivery without using virus, on the other hand, may have less risk of toxicity but, due to the low efficiency and low growth level, this method has not been widely adapted. Therefore, a method to deliver DNA physically and precisely to the limited target tissue or organ in situ may well decrease the difficulties to a large extent.

The particle delivery system (PDS) with the use of a shockwave is a method to deliver DNA into cells which is attached to particles of gold or tungsten which is harmless to cells, which is then accelerated to a speed higher the the speed of sound by the shockwave to pierce through the cell membrane, thus causing the DNA to be delivered into the cells. Investigations both in vitro and in vivo have proved that the DNA growth is sustained for a long period of time. Thus, the PDS is considered to serve most suitably as a means of gene therapy.

Conventionally, the mainstream of the PDS has been such that a burst of the compressed helium or nitrogen generates a shockwave, and metallic micro particles are accelerated by the high speed airflow behind the shockwave.

However, when the conventional PDS is redirected and applied from intravitam, especially intravascular therapy, to gene therapy, problems will arise such as troublesome handling of compressed gas and the hindering large size of the apparatus console.

OBJECTS AND SUMMARY OF THE INVENTION

The present invention is directed to solving these problems with the conventional PDS wherein the purpose is to provide a new method for generating a shockwave which allows miniaturization, better maneuverability and higher reliability and an apparatus thereby, a method for accelerating particles and an apparatus thereby, an apparatus for delivering drugs, a method for delivering DNA and an apparatus thereby.

The inventors of the present invention have developed a totally new DNA delivery apparatus by means of laser ablation and researched primarily on the possibility of gene therapy using the apparatus to treat obstructive cerebrovascular disease.

It is a feature of the present invention that, in order to achieve the above mentioned object, in the method for generating a shockwave, a short pulse energy, which is absorbed and causes vaporization and plasmatization of the metal, is applied on a surface of the metal foil, such that a jet is generated by a sudden expansion of the metal gas and wherein a shockwave is generated on the surface of the other side of the metal foil.

It is a feature of the present invention that the shockwave generating apparatus comprises a metal foil and an energy source which discharges short pulse energy which is applied on a side of the metal foil, thus absorbed and causes vaporization and plasmatization of the metal.

The short pulse energy of the shockwave generating apparatus according to the present invention is preferably light energy including but not limited to laser light energy or electrical energy which induces electric discharge between the energy source and the metal foil.

The energy source of the shockwave generating apparatus according to the present invention can preferably adjust one or more elements of the short pulse energy such as pulse width, strength waveform, the amount of energy, and energy density of the short pulse energy.

The thickness of the metal foil according to the present invention is preferably unequal, i.e., has a variable thickness.

The method for generating a shockwave and/or the shockwave generating apparatus according to the present invention has a capability to adjust a characteristic of the shockwave to be generated by changing the thickness of the metal used and/or the material of the metal used.

It is a feature of the present invention that, in the method for accelerating particles, a short pulse energy, which is absorbed and causes vaporization and plasmatization of the metal, is applied on the surface of the side of the metal foil, such that a jet is generated by a sudden expansion of the metal gas and thus a shockwave is generated on the surface of the other side of the metal foil, which then accelerates the micro particles located on the surface of the other side of the metal foil.

In the method for accelerating particles according to the present invention, the micro particles are comprised, for example, of inorganic substances including but not limited to metal, sapphire, diamond, alumina and garnet.

With the method for accelerating particles according to the present invention, the micro particles may be comprised of solid drugs.

It is a feature of the present invention that the apparatus for accelerating particles comprises the shockwave generating apparatus and a designated area for the micro particles to accelerate on the surface of the other side of the metal foil where the short pulse energy is applied.

It is a feature of the present invention that the apparatus for delivering drugs comprises the shockwave generating apparatus and a designated area for the micro particles of solid drugs to deliver into organism on the surface of the other side of the metal foil where the short pulse energy is applied.

It is a feature of the present invention that, in the method for delivering DNA, a short pulse energy, which is absorbed and causes vaporization and plasmatization of a metal, is applied on the surface of a side of the metal foil, such that a jet is generated by a sudden expansion of the metal gas and thus a shockwave is generated on the surface of the other side of the metal foil, which then accelerates the micro particles carrying DNA located on the surface of the other side of the metal foil to deliver DNA into organism cells.

The method for delivering DNA according to the present invention preferably delivers the micro particles carrying DNA into human body cells with the capability of adjusting the depth of its travel.

It is a feature of the present invention that the apparatus for delivering DNA comprises the shockwave generating apparatus and a designated area for the micro particles carrying DNA on the surface of the other side of the metal foil where the short pulse energy is applied.

According to the present invention, short pulse energy such as Q-switch laser light irradiated to a metal foil induces dissolution and, as a result of its reaction, a shockwave is generated in the metal foil. The shockwave is reflected on the surface of the other side of the metal foil as an expanded wave, thus the metal foil is deformed instantaneously and the micro particle on the metal foil is blasted off at an extremely high speed. This principle is simple so that the method is applied to almost all the area of human body with the use of endoscopes, thus such that a flexible and variable introduction of gene therapy can be achieved.

BRIEF DESCRIPTION OF THE DRAWINGS

The form of applying the present invention is described in conjunction with the accompanying drawings.

DETAILED DESCRIPTION OF THE INVENTION

Figure 1:
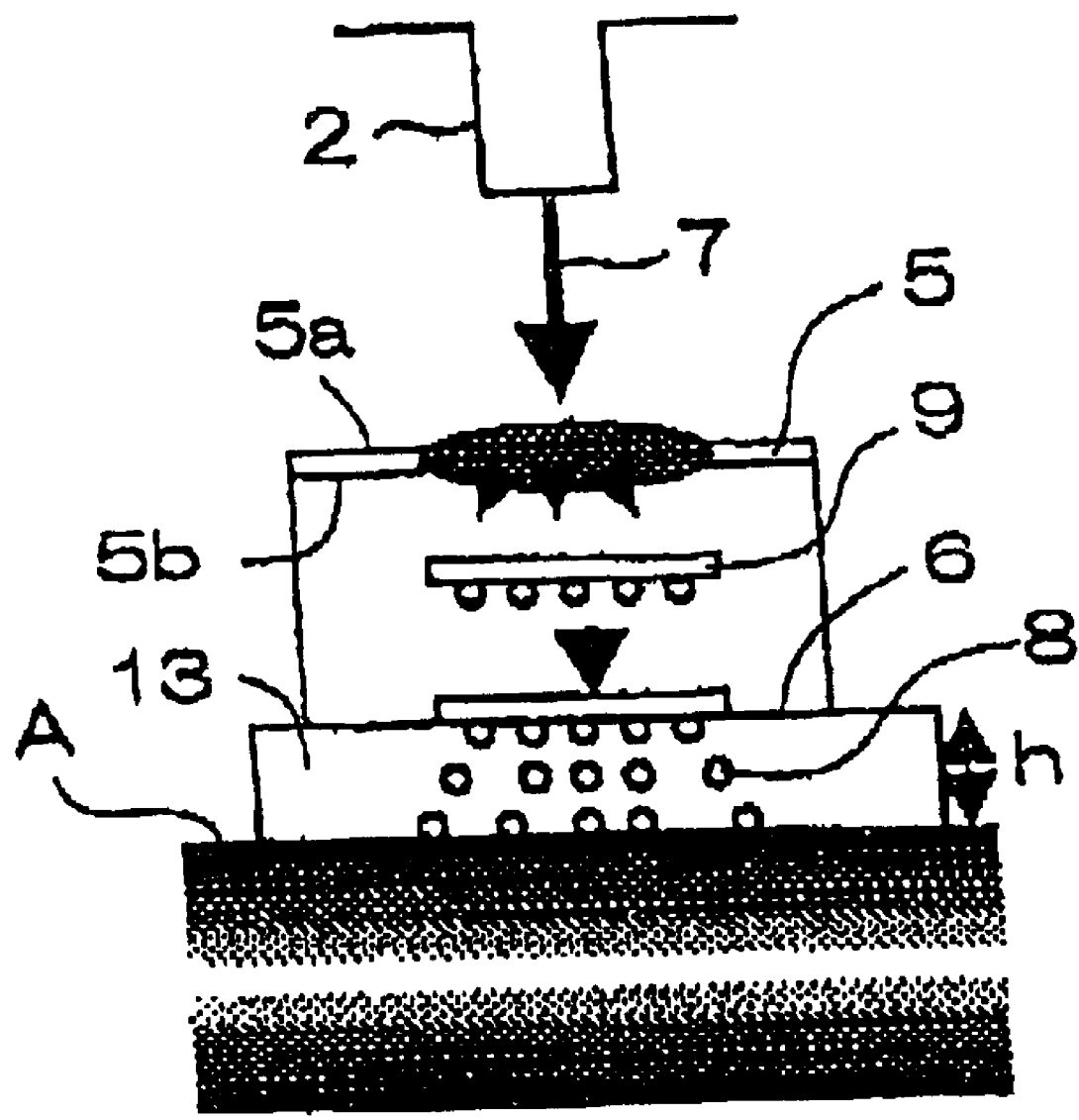
FIGS. 1, 2, 3(*a*), 3(B) and 3(C) are illustrative views of the form of applying the present invention.
Figure 2:
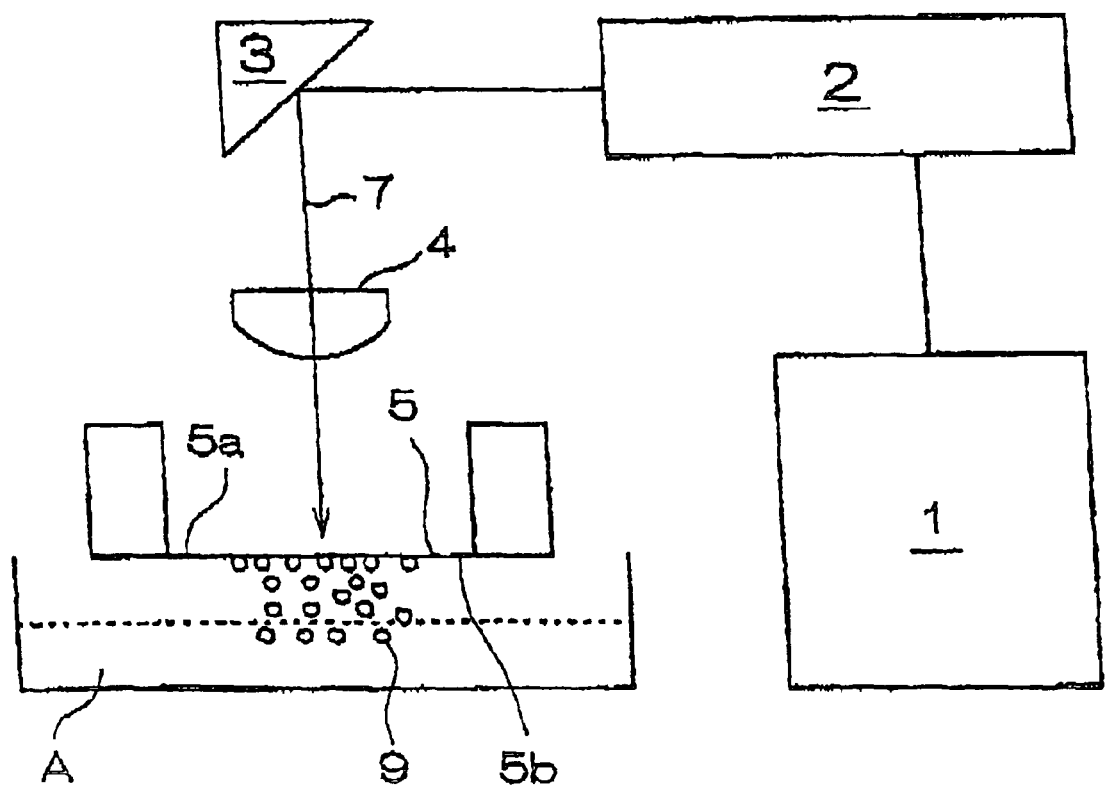

As shown in FIGS. 1 and 2, the shockwave generating apparatus comprises an electrical power source 1 for the laser, a Q-switch laser system 2, a refractive mirror 3, a lens 4, a metal foil 5 and a screen 6.

The shockwave generating apparatus operates such that the electrical power source 1 ignites the Q-switch laser system 2 to generate a laser beam 7, which is then reflected by a refractive mirror 3 and focused by a lens 4 to irradiate on the surface 5*a* of a side of a metal foil 5. The generated laser beam 7 is the short pulse energy which is absorbed and causes vaporization and plasmatization of the metal foil 5. The DNA delivery apparatus comprises the designated area for the micro particles 9 which carry DNA 8 on the surface 5*b* of the opposite side of the surface 5*a* where the laser beam 7 is irradiated. The metal foil 5 is placed so that the surface 5*b* faces toward an organism A at which the DNA 8 is aimed toward.

Figure 3:
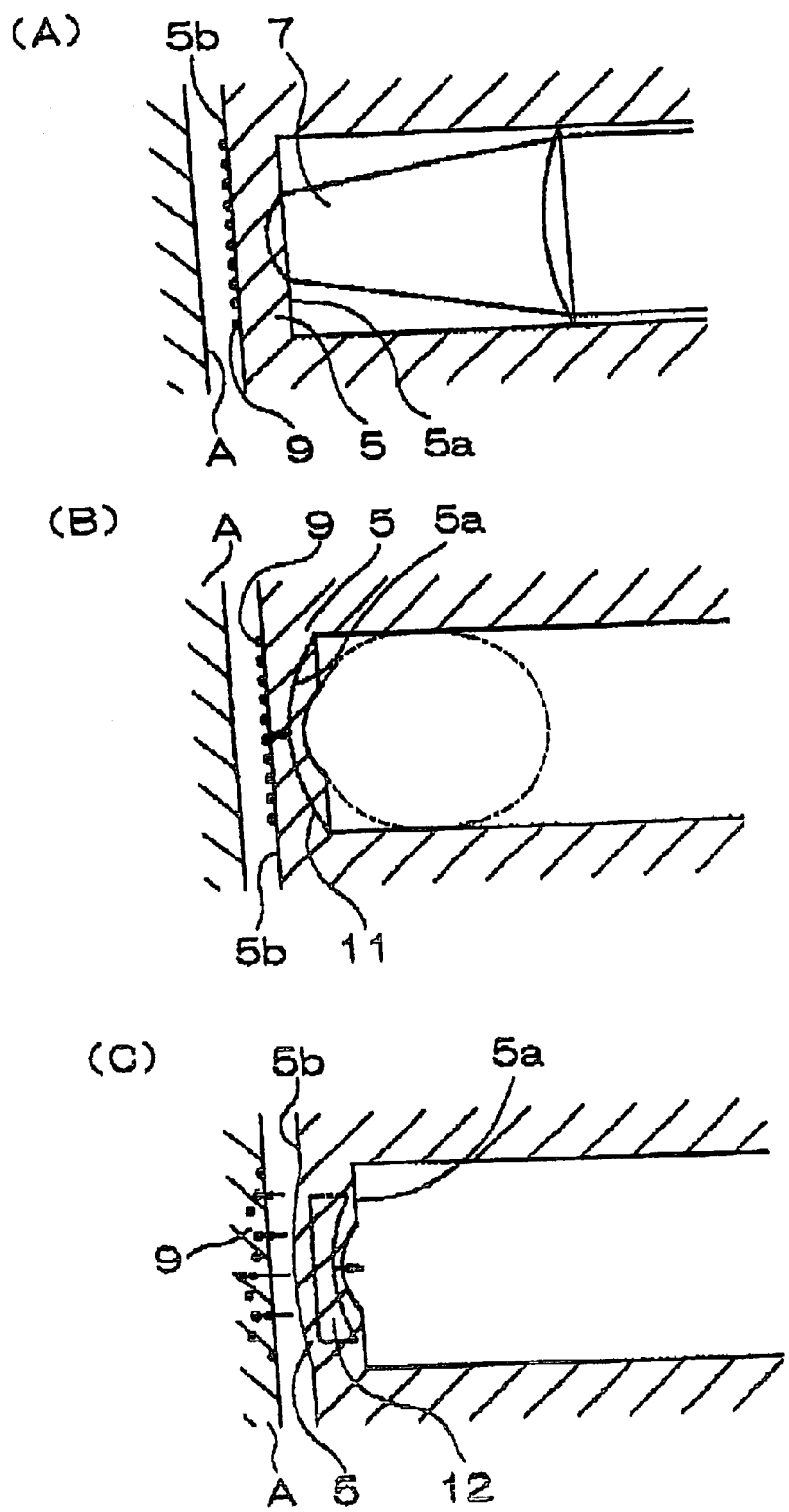

The DNA delivery apparatus is formed as illustrated in FIG. 3(A) so that the Q-switch laser beam 7 is irradiated to the metal foil 5 of 0.01 to 0.1 mm thick to form the spot of 2 to 3 mm in diameter with an even intensity distribution. The irradiation as illustrated in FIG. 3(B) generates a jet due to the instantaneous expansion of the metal gas, thus a plane shockwave 11 is easily created in the metal at a speed of 5 km/s with a diameter of 2 to 3 mm.

Separately and previously, the metal micro particles 9 of 1 micron in diameter which have been coated with DNA 8 are placed on the surface 5*b* of the opposite side of the surface 5*a* of the side of the metal foil 5 which the laser beam targets. As the shockwave reflects on the surface 5*b* on the opposite side of the metal foil 5 and turns into reflected wave 12, extremely high acceleration is generated on the surface 5*b*, which then accelerates the metal micro particle 9 on the surface 5*b*. As a result, as illustrated in FIG. 3(C), the metal micro particle 9 makes a free flight toward and through cells of organism A in order to physically deliver extraneous DNA 8 into the target cells.

In order to control the flight of the micro particle 9 or micro carrier, a screen 6 has previously been placed at a certain distance, 0.5 to 1.0 mm for instance, from the organism A. The relationship between the power of laser beam and the flight speed and the penetration depth is verified experimentally and numeric-analytically. When the apparatus is applied in vivo, a layer of carbon dioxide gas 13 is placed to secure free flight space between the organism A and tile metal foil 5 or the screen 6.

According to the DNA delivery apparatus, miniaturization of the apparatus can be realized to operate in conjunction with endoscopes of 2 mm or smaller in diameter. Thus, convenient and selective gene therapy for a narrow surgical site is achieved; prevention of post angioplasty restenosis is available and/or the bloodstream can be revived at a slow pace in order to avoid hyperperfusion syndrome due to abrupt revival of X bloodstream. In these cases, delivery of DNA intravascularly to the target area in a safe and precise manner can be achieved. Combination of the method for DNA delivery by a shockwave and intravascular technique can overcome various difficulties concerning DNA delivery to organism. The DNA delivery apparatus enables miniaturization of the apparatus comparatively with ease. It further enables control voluntarily over the direction of carrier particle to an extent.

The method for delivering DNA and the DNA delivery apparatus can be applied to prevent restenosis after percutaneous angioplasty for obstructive cerebrovascular disease, or to revive the bloodstream at a slow pace in order to avoid hyperperfusion syndrome due to abrupt revival of bloodstream. The method for delivering DNA and the DNA delivery apparatus further can be applied to many other diseases by changing DNA to deliver. For example, during brain tumor enucleation, DNA delivery can easily be conducted as a combination therapy to the surface of the cavity after the enucleation for the remaining tumor. Furthermore, in conjunction with endoscopes,gene therapy becomes available for tumors in the oral cavity or on the surface of bronchial tubes, or tumors in the digestive tract.

Furthermore, micro particles of solid drugs can be accelerated and delivered to organisms in place of S micro particle coated with DNA 8. Thus, it can be utilized not only as gene therapy for tumors but also as the method for delivering drug(s) or a drug delivery apparatus without an injection needle. The method for delivering DNA and the DNA delivery apparatus according to the form of applying the present invention can contribute to modern medicine and surgery tremendously. Especially research on gene therapy for obstructive cerebrovascular disease has yet rarely been reported both nationally and internationally. In the circumstances where the aging society is prevailing and cerebral apoplexy has been increasing, establishing a clinical application of the method is an urgent matter.

As illustrated in FIG. 2, a DNA delivery apparatus is operated and Q-switch Glass laser beam (wavelength 1.06 microns, pulse width 7 nsec, pulse energy 3.6 J) was irradiated with the spot of 2.0 mm in diameter to an aluminum foil. On the surface 5b on the opposite side of the surface 5a which the laser beam was irradiated, Si micro particles 9 of 20 microns in diameter are pasted. The result of the laser irradiation is that the shockwave was generated in the aluminum foil, thus the Si micro particles 9 were accelerated at the speed of 100 to 500m/sec and blasted off from the aluminum foil.

The present invention can provide miniaturization, maneuverability and reliability to a method and an apparatus for generating a shockwave, a method and an apparatus for accelerating particles, an apparatus for delivering drugs, and a method and an apparatus for delivering DNA.

What is claimed is:

1. A method for accelerating micro particles, comprising:

arranging the micro particles on a first surface of a metal foil, applying a short pulse energy to a second surface of the metal foil opposite to the first surface of the metal foil to be absorbed and cause vaporization and plasmatization of the metal foil, generating a jet by means of a sudden expansion of metal gas resulting from the vaporization and plasmatization of the metal foil, and thereby generating a shockwave on the first surface of the metal foil in order to accelerate the micro particles arranged on the first surface.

2. An apparatus for accelerating micro particles, comprising:

a metal foil having a first surface on which the micro particles are arranged and a second surface opposite to the first surface; and an energy source arranged to discharge short pulse energy on the second surface of said metal foil to be absorbed and cause vaporization and plasmatization of said metal foil which in turn causes a shockwave to be generated on the first surface of said metal foil which accelerates the micro particles on the first surface.

3. An apparatus for accelerating micro particles as claimed in claim 2, wherein said energy source is arranged to discharge laser light energy or electrical energy which induces electric discharge between said energy source and said metal foil.

4. An apparatus for accelerating micro particles as claimed in claim 2 or 3, wherein said energy source adjusts one or more elements of said short pulse energy including pulse width, waveform strength, amount of energy and energy density of said short pulse energy.

5. An apparatus for accelerating micro particles as claimed in claim 2 or 3, wherein said metal foil has a variable thickness.

6. A method for accelerating micro particles comprising:

applying a short pulse energy on a surface of a metal foil to be absorbed and cause vaporization and plasmatization of the metal foil, and generating thereby a jet by a sudden expansion of metal gas and a shockwave on a surface of an opposite side of the metal foil to accelerate micro particles located on the opposite side of the metal foil.

7. A method for accelerating particles as claimed in claim 6, wherein the micro particles comprise inorganic substances selected from a group consisting of metal, sapphire, diamond, alumina and garnet.

8. A method for accelerating particles as claimed in claim 6, wherein the micro particles comprise at least one solid drug.

9. An apparatus for accelerating micro particles as claimed in claim 2 or 3, wherein said metal foil includes a designated area for the micro particles on the first surface of said metal foil.

10. An apparatus for delivering micro particles of a solid drug, comprising:

an apparatus for accelerating micro particles as claimed in claim 2 or 3;

said metal foil including a designated area for the micro particles of the solid drug to be delivered into an organism on the first surface of said metal foil.

11. A method for delivering DNA comprising:

applying a short pulse energy on a surface of a metal foil to be absorbed to cause vaporization and plasmatization of the metal foil; and generating thereby, a jet by a sudden expansion of the metal gas and a shockwave on a surface of an opposite side of the metal foil to accelerate micro particles carrying DNA located on the surface of the opposite side of the metal foil to thereby deliver DNA into organism cells.

12. A method for delivering DNA as claimed in claim 11, wherein the micro particles carrying DNA are delivered into the organism cells with a capability of adjusting a depth of travel.

13. An apparatus for delivering DNA carried on micro particles, comprising:

an apparatus for accelerating micro particles as claimed in claim 2 or 3, said metal foil including a designated area for the micro particles carrying DNA on the first surface of said metal foil.

14. A method for delivering DNA as claimed in claim 11, further comprising forming the micro particles carrying DNA by coating DNA onto metal micro particles.

15. A method for delivering DNA as claimed in claim 11, further comprising arranging a screen between the metal foil and the organism cells to control flight of the micro particles.

* * * * *

UNITED STATES PATENT AND TRADEMARK OFFICE
CERTIFICATE OF CORRECTION

PATENT NO. : 6,767,743 B2 Page 1 of 1
DATED : July 27, 2004
INVENTOR(S) : Kazuyoshi Takayama et al.

It is certified that error appears in the above-identified patent and that said Letters Patent is hereby corrected as shown below:

<u>Title page,</u>
Insert Item -- [30]    Foreign Application Priority Data
           March 16, 2001    (JP)………………….. 2001-076376 --

Signed and Sealed this

Twenty-fifth Day of January, 2005

JON W. DUDAS
*Director of the United States Patent and Trademark Office*